United States Patent [19]

Mazurek et al.

[11] Patent Number: 5,637,703
[45] Date of Patent: Jun. 10, 1997

[54] DERIVATIVES OF GENISTEIN

[75] Inventors: Aleksander P. Mazurek, Warsaw, Poland; Krzysztof Biniecki, Mount Royal, Canada; Lech Kozerski, Warsaw, Poland

[73] Assignee: Drug Institute, Warsaw, Poland

[21] Appl. No.: 696,371

[22] Filed: Aug. 13, 1996

[30] Foreign Application Priority Data

Sep. 15, 1995 [PL] Poland ................. 310486

[51] Int. Cl.$^6$ ............. C07D 311/30; C07D 405/02; C07D 413/02
[52] U.S. Cl. .............. 544/109; 544/410; 544/376; 549/403
[58] Field of Search ............. 544/109, 410; 549/403

[56] References Cited

U.S. PATENT DOCUMENTS 4,713,465 12/1987 Krämer et al. ................. 549/403
4,788,215 11/1988 Krämer et al. ................. 549/403

Primary Examiner—Robert W. Ramsuer
Attorney, Agent, or Firm—Eugene Moroz; Mary J. Morry; Morgan & Finnegan

[57] ABSTRACT

The invention concerns chemical compounds, derivatives of genistein, which exhibit pronounced immunosuppressant and antitumor activity. In particular, the invention concerns compounds having general formula 1, where $R^1$, $R^2$, $R^3$ are the same or different, $R^1$ denotes hydrogen or alkyl, $R^2$ and $R^3$ are the same or different and denote hydrogen, alkyl or aryl, or $R^2$ and $R^3$ are taken together with the nitrogen to which they are connected to form a heterocycle ring.

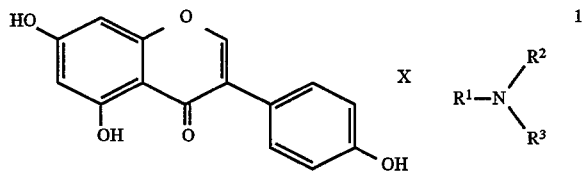

4 Claims, No Drawings

DERIVATIVES OF GENISTEIN

FIELD OF THE INVENTION

The invention concerns chemical compounds, derivatives of genistein, which exhibit pronounced immunosuppressant and antitumor activity.

BACKGROUND OF THE INVENTION

Genistein (4',5,7-trihydroxyisoflavone), is a naturally occurring plant hormone—phytoestrogen. It is well known that genistein specifically inhibits both protein kinase and DNA topoisomerase II.

French patent no. FR 2 693 724, describes 0-alkylated derivatives of genistein.

BRIEF DESCRIPTION OF THE INVENTION

The invention concerns compounds having general formula 1, where $R^1$, $R^2$, $R^3$ are the same or different, $R^1$ denotes hydrogen or alkyl, $R^2$ and $R^3$ are the same or different and denote hydrogen, alkyl or aryl, or $R^2$ and $R^3$ are taken together with the nitrogen to which they are connected to form a heterocycle ring.

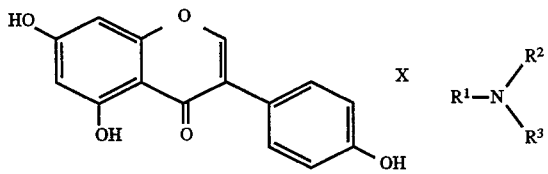

A preferred compound of general structure 1 is represented by formula 2, wherein $R^1$, $R^2$ and $R^3$ are identical and denote ethyl.

Another preferred compound of general structure 1 is represented by formula 3, wherein $R^1$ denotes hydrogen and $R^2$ and $R^3$ are connected and denote $CH_2CH_2OCH_2CH_2$.

Yet another preferred compound of general structure 1 is represented by formula 4, wherein $R^1$ denotes hydrogen and $R^2$ and $R^3$ are connected and denote $CH_2CH_2NHCH_2CH_2$.

The preferred compounds are shown below:

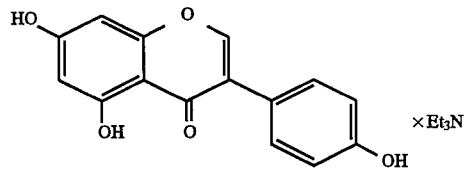

2: 4H-1-Benzopyran-4-one, 5,7-dihydroxy-3-(4-hydroxyphenyl), compound with triethylamine (1:1)—$C_{21}H_{25}NO_5$.

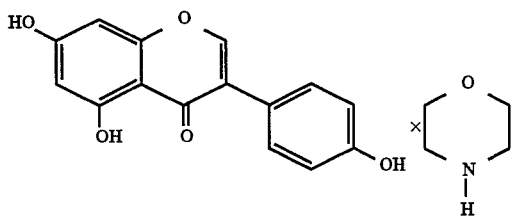

3: 4H-1-Benzopyran-4-one,5,7-dihydroxy-3-(4-hydroxyphenyl), compound with morpholine (1:1)—$C_{19}H_{19}NO_6$.

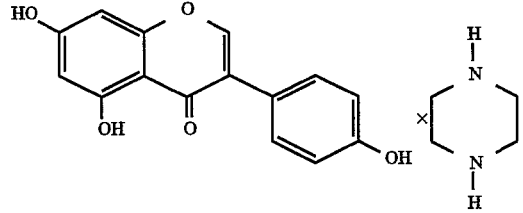

4: 4H-1-Benzopyran-4-one, 5,7-dihydroxy-3-(4-hydroxyphenyl), compound with piperazine (1:1)—$C_{19}H_{20}N_2O_5$.

DETAILED DESCRIPTION OF THE INVENTION

Compounds of general structure 1 are manufactured, according to the invention, by complexation reaction of genistein with amines in alcohol and crystallization of thus formed amine salts.

Compounds having structures 2, 3, 4 can appear in different forms depending on which of the phenolic groups is ionized and on the stoichiometric ratio of genistein and amine. Preferably this ratio is 1:1 and the OH group in position 7 is ionized.

It was found, according to the present invention, that compounds of general formula 1, preferably having structures 2, 3, or 4 exhibit immunosuppressant and antitumor activity in vitro. These antitumor and immunosuppressant activities are also expected in vivo; the latter being confirmed by our recent studies.

In addition, the preferable compounds exhibit improved physicochemical and immunosuppressant properties than genistein, i.e., greater solubility, long-term stability and activity.

Biological Assays

It was found, according to the invention, that compounds of the general structure 1, preferably having structures 2, 3, or 4, inhibit expression of activation-linked and differentiation markers of normal human lymphocytes exposed to Concanavalin-A ("Con-A").

Differentiation and activation markers on lymphocyte surfaces were established in 72 hr cell culture in the presence of Con-A and 80 µmoles of immunosuppressant. The amount of CD3, CD4, CD8, CD16+56, CD25, CD38, CD69, CD71 and HLADR positive lymphocytes were measured using the FACScan technique. The results were compared to control lymphocyte culture during the same time on culture medium and control culture with Con-A in a culture medium only.

In the cell culture experiments with immunosuppressant present statistically significant decrease of the amount of activated lymphocytes was found as compared to control culture experiments without immunosuppressant (p<0.001). The decrease of CD3, CD4, CD25, CD71 positive lymphocytes (0.7 to 1.7 fold) and smaller amount of CD2CD25, CD3CD71, CD4CD69, CD8CD38 positive lymphocytes (0.6 to 2.5 fold, respectively, p<0.0007) was observed, as compared to control lymphocytes Con-A stimulated without immunosuppressant. The survival time of lymphocytes in the presence of immunosuppressant and control lymphocytes was the same and was greater than 95%.

Potential applicability of compounds of general structure 1, preferably having structures 2, 3, or 4:

I. Human and veterinary medicine

Allotransplantation (within the same species)

Xenotransplantation (within different species)
Treatment of human immune system diseases
Oncology II. Cosmetic industry Plastic surgery
Wound healing
Skin growth Examples of the preparation and spectral characteristics of preferred compounds having structures 2, 3, and 4 are given below. These examples are exemplary of the present invention and incorporate suitable process parameters for use herein. These parameters may be varied, however, and the following should not be deemed limiting.

EXAMPLE 1

To a suspension of genistein (500 mg, 1.85 mmol) in methanol (10 ml) triethylamine (3 ml) was added while the reaction mixture was cooled with water. After 15 min. the excess of triethylamine and solvent were removed in vacuo. The resultant product 2 was dried in high vacuum. The yield was 680 mg.

IR (KBr): ν(cm$^{-1}$)=2454–3078 (br OH, NH), 1653 (C=O). $^1$H NMR (DMSO-d$_6$): δ (ppm)=0.97 (t, 9H, J=7.1 Hz), 2.57 (q, 6H, J=7.1 Hz), 6.16 (d, 1H, J=2.0 Hz), 6.32 (d, 1H, J=2.0 Hz), 6.78 end 6.82 (m, 2H, ½ AA'XX'), 7.33 end 7.38 (m, 2H, ½ AA'XX'), 8.26 (s, 1H), 12.9 (br s, 1H). $^{13}$C NMR (CDCl$_3$+DMSO-d$_6$) δ(ppm)=9.67, 44.69, 92.97, 98.52, 103.25, 114.17, 120.35, 121.71, 128.78, 151.24, 156.39, 156.81, 161.14, 164.76, 179.09.

EXAMPLE 2

To a suspension of genistein (305 mg, 1.13 mmol) in methanol (4.5 ml) morpholine (1 ml) was added dropwise while reaction mixture was cooled with water. Methanol and excess of morpholine were removed in vacuo. The resultant product was dissolved in chloroform with methanol (ca. 5%) and the product 3 was precipitated with hexane. After removal of the solvent the product 3 was dried in high vacuum. The yield was 285 mg.

IR (KBr): ν(cm$^{-1}$)=2479–3398 (OH, NH), 1656 (C=O). $^1$H NMR (CDCl$_3$+DMSO-d$_6$) δ(ppm)=2.72 (m, 4H), 3.52 (m, 4H), 6.14 (d, 1H, J=2.1 Hz), 6.25 (d, 1H, J=2.1 Hz), 6.75 end 6.79 (m, 2H, ½ AA'XX'), 7.24 end 7.29 (m, 2H, ½ AA'XX'), 7.93 (s, 1H). $^{13}$C NMR (CDCl$_3$+DMSO-d$_6$) δ(ppm)=45.28, 66.81, 93.20, 98.67, 104.15, 114.66, 120.73, 122.38, 129.18, 151.64, 156.75, 157.13, 161.62, 163.98, 179.75.

EXAMPLE 3

To a suspension of genistein (243 mg, 0.9 mmol) in methanol (12 ml) piperazine (77 mg, 0.9 mmol) was added and the mixture heated until dissolution of genistein. The reaction mixture was evaporated in vacuo and the residue was crystallized from a mixture of chloroform—ethanol (ca. 5:1). The yield of product 4 was 180 mg.

IR (KBr): ν(cm$^{-1}$)=3440 (br OH), 3247–2581 (br NH), 1657 (C=O). $^1$H NMR (CDCl$_3$+DMSO-d$_6$) δ(ppm)=2.71 (s, 8H), 6.14 (d, 1H, J=2.1 Hz), 6.24 (d, 1H, J=2.1 Hz), 6.75 end 6.79 (m, 2H, ½ AA'XX'), 7.22 end 7.27 (m, 2H, ½ AA'XX'), 7.84 (s, 1H). $^{13}$C NMR (CDCl$_3$+DMSO-d$_6$) δ(ppm)=43.77, 92.76, 98.55, 101.53, 113.49, 119.89, 120.64, 128.28, 150.67, 155.88, 156.42, 160.42, 167.07, 178.00.

$^1$H NMR spectra (200 MHz) were calibrated vs. DMSO signal (2.49 ppm), and $^{13}$C NMR spectra vs. CDCl$_3$ signal (77.0 ppm). The signal integrations may differ due to stoichiometric ratio of genistein—amine varying from 1:1.

Modifications of the above described modes for carrying out the invention that are obvious to those of skill in the fields of immunology, chemistry, medicine, and related fields are intended to be within the scope of the following claims.

We claim:

1. A compound having the general formula 1,

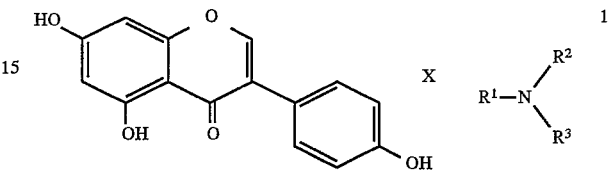

wherein $R^1$, $R^2$, $R^3$ are the same or different, and wherein $R^1$ denotes hydrogen or alkyl, and wherein $R^2$ and $R^3$ are the same or different and denote hydrogen, alkyl or aryl, or $R^2$ and $R^3$ are taken together with the nitrogen to which they are connected to form a heterocycle ring.

2. A compound according to claim 1, represented by formula 2,

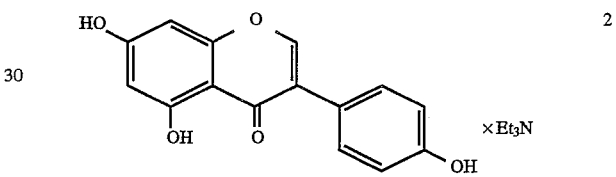

wherein in general formula 1, $R^1$, $R^2$, and $R^3$ are identical and denote ethyl.

3. A compound according to claim 1, represented by formula 3,

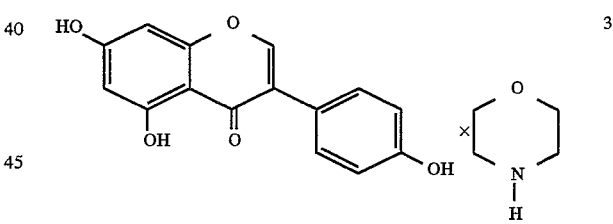

wherein in general formula 1, $R^1$ denotes hydrogen and $R^2$ and $R^3$ are connected and denote $CH_2CH_2OCH_2CH_2$.

4. A compound according to claim 1, represented by formula 4,

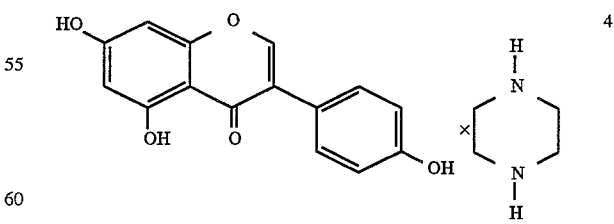

wherein in general formula 1, $R^1$ denotes hydrogen and $R^2$ and $R^3$ are connected and denote $CH_2CH_2NHCH_2CH_2$.

* * * * *